US00PP27976P3

(12) United States Plant Patent
Kordes

(10) Patent No.: US PP27,976 P3
(45) Date of Patent: May 9, 2017

(54) SHRUB ROSE PLANT NAMED 'KORAPFHECKI'

(50) Latin Name: *Rosa hybrida*
Varietal Denomination: KORapfhecki

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop ( * ) Notice: Subject to any disclaimer, the term of this patent is extended or adjusted under 35 U.S.C. 154(b) by 38 days.

(21) Appl. No.: 14/756,360

(22) Filed: Sep. 1, 2015

(65) Prior Publication Data
US 2017/0064888 P1 Mar. 2, 2017

(51) Int. Cl.
*A01H 5/02* (2006.01)

(52) U.S. Cl.
USPC ..... Plt./105

(58) Field of Classification Search
USPC ..... Plt./105
See application file for complete search history.

*Primary Examiner* — Keith Robinson

(57) ABSTRACT

'KORapfhecki' is a new and distinct variety of *Rosa hybrida* which is characterized by the combination of an upright and bushy growth habit, medium-sized double flowers which are orange in color and also attractive foliage with excellent disease resistance. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORapfhecki'.

BACKGROUND OF THE INVENTION

The present invention relates to a new and distinct *Rosa hybrida*, shrub rose cultivar, which has been given the variety denomination of 'KORapfhecki'. Its market class is PLT/102.

Parentage: The *Rosa hybrida* variety 'KORapfhecki' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent orange flowers;
3. Attractive and abundant glossy foliage; and
4. Resistance to diseases encountered in landscapes and gardens.

This combination of qualities is not present in prior rose cultivars known to the inventor. These objectives have been substantially achieved and in that distinguish 'KORapfhecki' from all other varieties known to the inventor.

'KORapfhecki' is a seedling selection which resulted from the controlled pollination of an unnamed breeding line, the seed parent, developed and owned by the same inventor and *Rosa hybrida* 'INTERfluco' (unpatented), the pollen parent, during the summer of 2002.

As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2003 from the seedling beds due to its superior characteristics and asexually propagated for further evaluation. This new and distinctive rose variety was given the name 'KORapfhecki'.

Asexual Reproduction: The first asexual propagation of 'KORapfhecki' was performed in July of 2003 at the inventor's nursery in Offenseth-Sparrieshoop, Germany. Subsequently, 'KORapfhecki' has been successfully propagated by stem cuttings and grafting in Jackson County, Oreg. These initial and other subsequent propagations conducted in controlled environments demonstrate that 'KORapfhecki' reproduces true to type in successive generations of asexual reproduction.

SUMMARY OF THE INVENTION

The following characteristics have been repeatedly observed and represent the distinguishing characteristics of the new *Rosa hybrida* cultivar 'KORapfhecki'. These traits, in combination, distinguish 'KORapfhecki' as a new and distinct cultivar.

1. *Rosa hybrida* 'KORapfhecki' exhibits an upright, bushy growth habit; and
2. *Rosa hybrida* 'KORapfhecki' exhibits an abundance of flowers; and
3. *Rosa hybrida* 'KORapfhecki' exhibits a semi-double flower habit; and
4. *Rosa hybrida* 'KORapfhecki' exhibits a medium flower size; and 5. *Rosa hybrida* 'KORapfhecki' exhibits an orange flower color, at anthesis; and
6. *Rosa hybrida* 'KORapfheck' exhibits dark green, glossy foliage; and
7. *Rosa hybrida* 'KORapfhecki' exhibits very high disease resistance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORapfhecki', taken from plants of three years of age.

DETAILED BOTANICAL DESCRIPTION

The following is a detailed botanical description of a new and distinct variety of *Rosa hybrida* known as 'KORapfhecki', based upon field observations made in June of 2015 from three year old plants, grown in-ground, at a nursery in Jackson County, Oreg.

Those skilled in the art will appreciate that certain characteristics will vary with older or, conversely, with younger plants. 'KORapfhecki' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORapfhecki' and comparisons with other varieties of *Rosa hybrida* are provided below.

General plant description:

*Growth rate*.—Moderate.

*Growth habit*.—Upright and bushy.

*Mature dimensions*.—Approximately 155 cm tall and 60 cm wide.

*Cold hardiness*.—USDA Hardiness Zones 5 to 9.

*Propagation*.—Grafting and stem cuttings.

*Disease resistance*.—Average resistance to powdery mildew (*Sphaerotheca pannosa*) and a high degree of resistance to blackspot (*Diplocarpon rosae*) and rust (*Phragmidium* sp.) diseases under normal growing conditions in Jackson County, Oreg.

Root system: Fibrous.

Stems:

*Stem color*.—Immature stems are Yellow-Green Group 144B; mature stems are Yellow-Green Group 144A.

*Anthocyanin intonations*.—Greyed-Purple Group 184C.

*Stem surface texture*.—The surfaces of both immature and mature stems are smooth.

*Stem dimensions*.—Typical mature stems are approximately 100 cm long and 6 to 9 mm in diameter near the base.

*Prickles*.—Incidence — Present, primarily on mature stems; 0 to 2 prickles per 10 cm of stem, on average. Size — Average length is 3 to 5 mm. Immature prickle color — Yellow-Green Group 145B. Mature prickle color — Yellow-Green Group 145B. Anthocyanin intonations — Greyed-Purple Group 184C. Shape — Concave. Texture — Smooth.

Leaves:

*Arrangement*.—Imparipinnate compound leaves; mature axillary leaves consisting of 5 leaflets.

*Attachment*.—Petiolate.

*Dimensions*.—150 to 160 mm long and 110 to 130 mm wide.

*Abundance*.—Average.

*Stipules*.—Size — 27 mm long and 5 mm wide. Stipule color — Yellow-Green Group 144B. Anthocyanin intonations — Greyed-Purple Group 184C; present on stipitate glands and the adaxial surface of the midrib. Stipitate glands — Abundant; only present at margins. Margins — Glandular toothed. Texture, adaxial surface — Glabrous. Texture, abaxial surface — Glabrous. Apex — Apiculate. Base — Winged.

*Petiole*.—Length — Average 40 to 45 mm. Diameter — Average 1.5 mm. Petiole color, adaxial surface — Yellow-Green Group 144A. Petiole color, abaxial surface — Yellow-Green Group 145A. Margins — Glandular toothed. Anthocyanin intonations — Greyed-Purple Group 187C on stipitate glands. Prickles — One small prickle occasionally present. Stipitate glands — Limited number present on margins. Texture, adaxial surface — Papillate. Texture, abaxial surface — Glabrous. Strength — Moderately strong.

*Rachis*.—Length — Average 10 to 25 mm. Diameter — Average 1.5 to 2 mm. Color, adaxial surface — Yellow-Green Group 144A. Color, abaxial surface — Yellow-Green Group 145A. Anthocyanin intonations — None observed. Margins — Entire, with occasional stipitate glands. Texture — Glabrous. Prickles — A few small prickles underneath. Stipitate glands — Limited numbers of stipitate glands at margins.

*Leaflets*.—Quantity — Normally 5 leaflets present on leaves in middle of the stem. Dimensions — Average size of the terminal leaflet is 75 mm long and 45 mm wide. Shape — Elliptical. Apex — Acuminate. Base — Cuneate. Margins — Serrated and undulating. Texture, adaxial surface — Glossy and leathery. Texture, abaxial surface — Matte and leathery. Juvenile foliage color, adaxial surface — Yellow-Green Group 144A. Juvenile foliage color, abaxial surface — Yellow-Green Group 144B. Mature foliage color, adaxial surface — Green Group 137A. Mature foliage color, abaxial surface — Yellow-Green Group 146B. Anthocyanin intonations — Greyed-Purple Group 187C. Present at and near the margins of juvenile foliage. Venation — Reticulate. Petiolule — Dimensions — 1 to 2 mm long and 1 mm in diameter. Petiolule color, adaxial and abaxial surfaces — Yellow-Green Group 145C. Anthocyanin intonations — Greyed-Purple Group 184C. Prickles — None present. Stipitate Glands — A few stipitate glands present along margins. Texture, adaxial surface — Smooth with fine hairs present. Texture, abaxial surface — Smooth and glabrous.

Inflorescence:

*Inflorescence type*.—Both compound corymbs with multiple flowers and solitary flowers observed.

*Blooming habit*.—Recurrent.

*Quantity of flowers*.—Generally 1 to 4, on corymbs.

*Size*.—Corymbs are 130 mm tall and 130 mm wide, on average.

*Peduncle*.—Surface — Lacking stipitate glands and prickles. Length — 25 to 50 mm average length. Diameter — 3 to 4 mm average diameter. Color — Yellow-Green Group 144A. Anthocyanin intonations — Not present. Texture — Glabrous. Strength — Strong.

Flowering laterals: Present below the initiation of inflorescence. Generally 6 flowering laterals are present, with 10 flowers per flowering shoot.

Bud:

*Bud form*.—Long. Pointed ovoid.

*Size*.—Upon opening, 30 mm in length from base of receptacle to distal end of bud and 18 mm diameter at its widest point.

*Texture*.—Leathery.

*Color, as sepals first unfold*.—Red Group 52A.

*Color when one-quarter open, upper surface*.—Marginal zone — Orange-Red Group 33B. Middle zone — Orange-Red Group 33C. Basal zone — Yellow Group 9A.

*Color when one-quarter open, lower surface*.—Marginal zone — Red Group 41C. Middle zone — Red Group 41C. Basal zone — Yellow Group 5B.

Flower:

*Pedicel*.—Surface — Glabrous, with stipitate glands present. Length — 35 to 50 mm, on average. Diameter — 2 to 3 mm, on average. Color — Yellow-Green Group 144B. Anthocyanin intonations — Greyed-Purple Group 187C on stipitate glands. Strength — Weak. Texture — Papillate.

*Sepals*.—Diameter of calyx — 25 to 30 mm, at anthesis. Color, adaxial surface — Greyed-Green Group 194B. Color, abaxial surface — Yellow-Green Group 144A. Anthocyanin intonations — Greyed-Purple 187C. Size — 25 mm long and 7 to 10 mm wide, on average. Shape — Weak foliaceous appendages on 3 of the 5 sepals. Apex — Apiculate. Base — Flat at union with receptacle. Quantity — Five. Texture, adaxial surface — Hoary. Texture, abaxial surface — Leathery. Margins — Cilliate and glandular toothed observed. Stipitate glands — Limited; along margins.

*Corolla*.—General shape of corolla — Cup-shaped and open; round. Shape of corolla when viewed from the side — Upon opening, upper portion — Flat. Upon opening, lower portion — Flattened convex. Open flower, upper portion — Flattened convex. Open flower, lower portion — Concave. Aspect — Flowers held upright. Dimensions — Small for a shrub rose. When open, the average flower diameter is 45 to 60 mm and the average flower height is 30 mm. Fragrance — Light. Duration — On the plant 5 days. Senesced petals drop away cleanly. Petals — Petal arrangement — Not formal. Petal count — Exhibits double flowers with approximately 25 petals under normal conditions. Petal reflex — Petals are somewhat reflexed. Petal reflex occurs one by one, with outer petals reflexing first. Petal margin — Entire. Petal shape — Obovate. Apex — Obtuse. Base — Cuneate. Dimensions — Approximately 25 to 30 mm long and 20 to 34 mm wide. Texture, inner surface — Smooth. Texture, outer surface — Smooth. Petal color, upon opening — Outermost petals, outer surface — Marginal zone — Red Group 52D. Middle zone — Orange-Red Group 33C, with occasional intonations of Yellow Group 6C on the midrib. Basal zone — Yellow Group 6C. Outermost petals, inner surface — Marginal zone — Red Group 52D. Middle zone — Orange Group 25B. Basal zone — Yellow Group 9A. Innermost petals, outer surface — Marginal zone — Orange-Red Group 33C. Middle zone — Orange-Red Group 33C, with occasional intonations of Yellow Group 6C on the midrib. Basal zone — Yellow Group 6C. Innermost petals, inner surface — Marginal zone — Orange Group 25B. Middle zone — Orange Group 25B. Basal zone — Yellow Group 9A. Petal color, after opening — Outermost petals, outer surface — Marginal zone — Red Group 52C. Middle zone — Orange-Red Group 33C, with occasional intonations of Yellow Group 6C on the midrib. Basal zone — Yellow Group 6C. Outermost petals, inner surface — Marginal zone — Red Group 52B. Middle zone — Orange Group N25B, with occasional intonations of Yellow Group 9A on the midrib. Basal zone — Yellow Group 9A. Innermost petals, outer surface — Marginal zone — Orange-Red Group 33C. Middle zone — Orange-Red Group 33C, with occasional intonations of Yellow Group 6B on the midrib. Basal zone — Yellow Group 6B. Innermost petals, inner surface — Marginal zone — Orange Group N25B. Middle zone — Orange Group N25B, with occasional intonations of Yellow Group 9A on the midrib. Basal zone — Yellow Group 9A. General Tonality — Orange-Red Group 30D, at anthesis, and fading to Orange Group 25D.

*Petaloids*.—Quantity — 10 petaloids per flower, on average. Dimensions — Approximately 10 to 20 mm long and 7 to 15 mm wide. Color, inner surface — Orange-Red Group 33A, with intonations of Yellow Group 6A along the midrib. Color, outer surface — Orange-Red Group 33B, with intonations of Yellow Group 6A along the midrib. Texture, inner surface — Smooth. Texture, outer surface — Smooth. Margins — Undulated. Shape — Spatulate. Apex — Obtuse and emarginate. Base — Attenuate.

Reproductive organs:

*Stamens*.—Quantity — Approximately 110, on average, and regularly arranged around the styles. Anthers — Dimensions — 1 to 1.5 mm long and 1 mm wide, on average. Color — Yellow-Orange Group 16D. Pollen — Generally present; abundant. Pollen Color — Greyed-Orange Group N163C. Filaments — Color — Yellow Group 12A. Length — 4 mm.

*Pistils*.—Quantity — Average; approximately 75 present. Stigmas — Dimensions — 1 mm long and 1 mm wide. Location — Equal in position to anthers. Color — Yellow Group 12A. Styles — Length — Approximately 4 mm long. Color — Green-White Group 157B with intonations of Red Group 52B.

*Ovary*.—Dimensions — 3 mm long and 1 mm in diameter. Color — Green-White 157C.

*Receptacle*.—Shape — Urn-shaped. Dimensions — Approximately 5 mm high and 7 mm wide. Surface — Glaucous, with a limited number of fine hairs present. Color — Yellow-Green Group 144B with intonations of Greyed-Purple Group 187C. Texture — Smooth.

Hips and seed formation: Not observed.

COMPARISONS WITH THE PARENTS

The new rose plant may be distinguished from its seed parent, an unnamed seedling, by the following combination of characteristics:

1. 'KORapfhecki' exhibits an orange flower color, whereas the unnamed seedling exhibits a yellow flower color.
2. 'KORapfhecki' exhibits an upright and bushy growth habit, whereas the unnamed seedling exhibits a spreading growth habit.

The new rose plant may be distinguished from its pollen parent, *Rosa hybrida* 'INTERflocu', by the following combination of characteristics:

1. 'KORapfhecki' exhibits a medium flower size, whereas 'INTERflocu' exhibits a large flower size.
2. 'KORapfhecki' exhibits very high disease resistance, whereas 'INTERflocu' exhibits average disease resistance.

COMPARISONS WITH SIMILAR *ROSA HYBRIDA* CULTIVARS KNOWN TO THE INVENTOR

For a comparison, several physical characteristics of the rose variety 'KORburox', a rose variety from the same inventor described and illustrated in U.S. Plant Pat. No. 23,121 are compared to 'KORapfhecki' in Chart 1.

CHART 1

| Characteristic | 'KORapfhecki' | 'KORburox' |
|---|---|---|
| General tonality of flower, at anthesis. | Orange-Red Group 30D. | Red Group 53B. |
| Average Plant Height. | 155 cm. | 60 cm. |
| Bud color as sepals first unfold. | Red Group 52A. | White Group N155B. |

That which is claimed:

1. A new and distinct variety of rose plant named 'KORapfhecki', as described and illustrated herein.

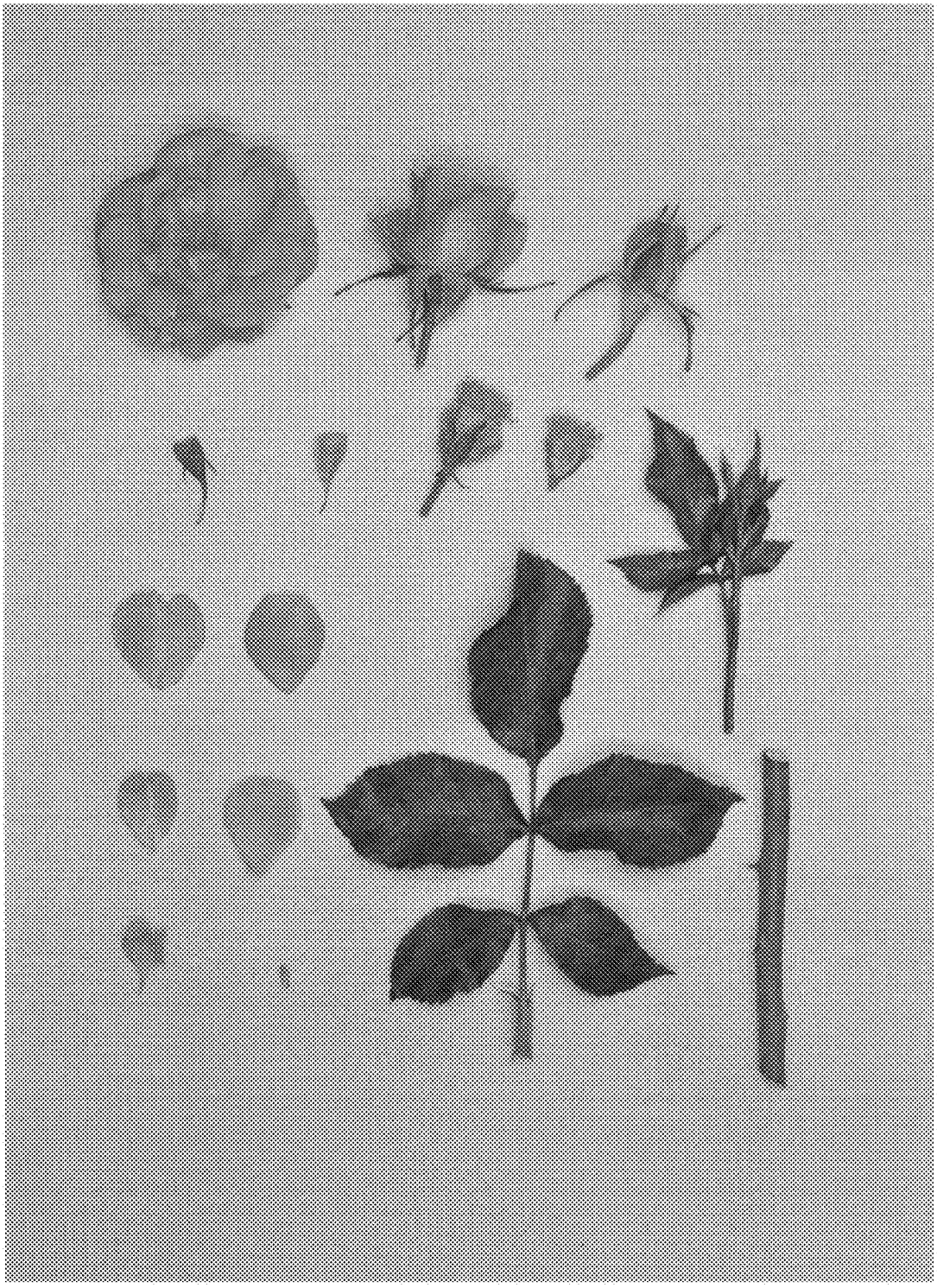

* * * * *